United States Patent [19]

Gordon et al.

[11] Patent Number: 5,134,074

[45] Date of Patent: Jul. 28, 1992

[54] EMBRYOGENIC CALLUS AND CELL SUSPENSIONS OF CORN INBRED B73

[75] Inventors: Phillip N. Gordon, Old Lyme; Thomas B. Rice, Niantic, both of Conn.

[73] Assignee: DeKalb Plant Genetics, DeKalb, Ill.

[21] Appl. No.: 500,231

[22] Filed: Mar. 23, 1990

Related U.S. Application Data

[63] Continuation of Ser. No. 877,033, Jun. 20, 1986, abandoned.

[51] Int. Cl.$^5$ ............... C12N 5/00; C12N 5/02
[52] U.S. Cl. ............... 435/240.4; 435/240.46; 435/240.49; 435/240.5; 435/240.31
[58] Field of Search ........... 435/240.4, 240.46, 240.49, 435/240.5, 240.51; 800/200, 235, 250, DIG. 56

[56] References Cited

U.S. PATENT DOCUMENTS 4,665,030 5/1987 Close .................... 435/240.45
4,666,844 5/1987 Cheng .................... 800/1

OTHER PUBLICATIONS

Meadows, M. 1982/1983 Plant Sci. Lett. 28:337–348.
Lu et al. 1982, Theor. Appl. Genet. 62:109–112.
Gengenbach et al. 1977, Proc. Natl. Acad. Sci. USA 74(11):5113–5117.
Green, C. 1982, p. 107–108 IN: Plant Tissue Culture 1982, Fujiwara, A. (ed.), Maruren Co., Ltd., Tokyo.
Potrykus et al, 1979, Theor. Appl. Genet. 54:209–214.
Green et al. 1975, Crop Sci. 15:417–421.
Green et al. (1974) Crop Sci. 14:54–58.
Lu et al (1983) Theor. Appl. Genet 66:285–89.
Ozias-Akins P, "Progress and Limitations in the Culture of Cereal Protoplasts", Trends in Biotechnology 2(5), 1984, 119–123.
Rhodes, C. A. et al, "Plant Regeneration From Protoplasts Isolated from Embryogenic Maize Cell Cultures", Biotechnology Jun. 6, 1988, 56–60.
D. A. Evans, "Somaclonal Variation–Genetic Basis an Breeding Applications", Trends Genet 5(2), 1989, 46–50.
Ludwig, S. R. et al, "High Frequency Callus Formation from Maize Protoplasts", Theos Appl. Genetics (1985) 71 344–50.

*Primary Examiner*—David T. Fox
*Attorney, Agent, or Firm*—Arnold, White & Durkee

[57] ABSTRACT

Embryogenic callus of corn inbred B73 is disclosed along with viable, seed-producing plants derived from this embryogenic callus. Also disclosed are plantlets from embryogenic cell suspension cultures of B73 and mutants and recombinant progeny of embryogenic callus.

3 Claims, No Drawings

EMBRYOGENIC CALLUS AND CELL SUSPENSIONS OF CORN INBRED B73

This is a continuation of application Ser. No. 877,033, filed on Jun. 20, 1986, now abandoned.

BACKGROUND OF THE INVENTION

*Zea mays* L. or corn is a major worldwide cereal crop. In the continental United States alone, an estimated 82 million acres of corn is planted yearly. A survey of the U.S. corn germplasm base conducted in 1979 accounting for 1.3 billion pounds of seed corn, determined that corn inbred B73 was used in the production of approximately 178.5 million pounds of corn hybrid seed. This amount reflects approximately 14% of the total corn seed required for the 1980 planting of 82 million acres of corn in the United States. B73 was used to produce more hybrid corn seed than any other corn inbred line in the 1979 survey. As the major inbred corn line used in hybrid corn seed production, B73 is a commercially important corn inbred. Successful efforts to improve B73 are likely to have a major impact on the commercial corn seed business.

Current methods for improving inbred corn lines are time consuming, labor intensive, and risky. Thus, methods that reduce any of these problems would represent an advance in the cereal breeding arts. One method for inducing changes in an inbred corn seed line is accomplished by exposing inbred seed corn to a mutagen, which may be ionizing radiation or a mutagenic chemical, growing the seed out, and screening the corn plants for a desired characteristic such as decreased height or pathogen resistance. Seed from plants displaying the desired characteristics are then replanted, rescreened and the seed from plants passing the screen are retained. After several years and many grow-outs of the seed, a sufficient seed stock of the inbred displaying the desired characteristic is accumulated for commercial breeding.

Several problems attend the method of obtaining a modified inbred corn seed line as described above. Inbred corn lines are highly homozygous, or pure-bred. Such inbred lines frequently display low vigor, and as a result frequently produce few seed. If seed production is too low, successful large-scale production of seed derived from a single plant of a modified inbred line may not be possible at all. Even if the modified inbred is vigorous and produces numbers of fertile seed, several years and many acres of land are required to produce enough seeds to make commercial breeding possible.

Other approaches to the propagation of desirable modified inbreds have also been suggested and rely upon plant tissue culture techniques. In some of these approaches, cell cultures are subjected to mutagenic ionizing radiation. The desirable characteristic is selected or screened in cell culture. Cells having the desirable characteristic are propagated in culture and ultimately regenerated to form seed-bearing plants (see e.g., Bottino P. J., "The Potential of Genetic Manipulation of Plant Cell Cultures for Plant Breeding," *Radiation Botany*, 15:1-16 (1975).

The feasibility of using selection techniques on callus cultures of certain non-commercial corn inbreds and the regeneration of plants producing seed that carry the characteristic selected in tissue culture has been demonstrated by Hibberd et al. (see, "Selection and Characterization of a Feedback-Insensitive Tissue Culture of Maize," *Planta*, 148:183-187 (1980).)

Prior to the development of the embroygenic callus line of corn inbred B73 of the instant invention, no friable embryogenic callus culture or embryogenic cell suspension culture of a commercially significant inbred corn line has been described. With respect to embryogenic callus lines of noncommercial corn inbreds, C. E. Green has described a friable callus of corn inbred A188 capable of regenerating plants by somatic embroygenesis (see, Green, C. E., "Somatic Embroygenesis and Plant Regeneration From the Friable Callus of *Zea mas* L." in Proc. 5th Int'l. Cong. Plant Tissues and Cells, Akio Jujiware ed., Japanese Association of Plant Tissue Culture, pub. Tokyo, Japan, 1982). Embryogenic friable A188 callus according to Green can be derived from spontaneous sectors of organogenic callus.

Green's embryogenic callus appears undifferentiated, highly friable, has little organization on visual inspection and is fast growing, requiring sub-culturing at least every two weeks. The embryogenic callus culture described by Green develops to the coleoptilar stage on MS or N6 medium with 2% sucrose and 0.5 to 1.0 mg/l 2,4-D. Normal development to the mature embryo stage is possible if the embryos are transferred to N6 medium with 6% sucrose and no 2,4-D. The mature embryo can then be induced to germinate on MS or N6 medium containing 2% sucrose without hormones.

Green also described suspension cultures of the embryogenic lines of A188 and disclosed that such suspension cultures can be maintained in MS medium containing 1 mg/1 2,4-D with 2% sucrose. When aliquots of the suspension cultures are plated onto solidified MS medium containing 2% sucrose, a callus forms from the plated suspensions and embryos form on the callus surface. These embryos are transferred to MS or N6 medium with 6% sucrose for further development. After 2 weeks on medium with 6% sucrose these are transferred to low sucrose, hormone-free medium for embryo generation. A188 plants may be routinely regenerated from these embryos.

A non-regenerating cell line of corn inbred B73 is known (see Potrykus et al, *Theoretical Applied Genetics*, 54:209, 1979). This cell line in suspension culture was established from a primary culture of protoplasts from plant tissues of the B73 inbred. The cells are characterized as growing well in suspension culture and easily maintainable on agar medium. Furthermore, the cells can be enzymatically turned into protoplasts, which in turn regenerate walls and become proliferating cells again. Significantly, the cells of this line have never been induced to regenerate plants and moreover display ploidy abnormalities, a characteristic well known in other non-regenerating diploid plant cell lines. (See M. G. Meadows, "Characterization of Cells and Protoplasts of the B73 Maize Cell Line " *Plant Science Letters*, 28:337-348(1982/83). Other attempts to achieve plant regeneration from established B73 callus have been similarly unsuccessful. (See Bartkowiak, E., "Tissue Culture of Maize Plantlet Regeneration From Scutella Callus," *Genetica Polonica*, Vol. 23:93-101 (1982)).

The ability to culture somatic cells of inbred plants in vitro enables the plant breeder to apply the techniques of microbial genetics to specific breeding problems in crop plants. Included in the genetic approaches that have application to plant breeding are: selection of mutations in cell cultures, studying host-pathogen interrelationships, transfer of genetic information into cells through uptake of exogenous heterologous (see Szoka et al., U.S. Pat. No. 4,394,448) or homologous (see IPRI European Patent Application No. 90033A) DNA. Furthermore, somatic cell culture enables the plant breeder to develop, select and propagate somaclonal variants having novel or useful agronomic characteristics.

The major obstacle to the application of these techniques to commercial corn inbred B73 and some other commercial inbreds has, until now, been the inability to provide a tissue culture or cell suspension that can regenerate whole plants. The embryogenic corn callus line and corn cell line derived therefrom provided by the instant invention makes it possible to apply somatic cell genetic techniques to a major commercial corn line for the first time. The particular uses to which a cereal, and particularly a corn cell line such as the one described herein, can be put are outlined in numerous articles (see e.g., Bottino, P. J. "Potential of Genetic Manipulation in Plant Cell Culture," *Radiation Botany*, Vol 15:1–16 (1975) and Vasil, I. K., "Plant Cell Culture and Somatic Cell Genetics of Cereals and Grasses," *Plant Improvement and Somatic Cell Genetics*, Vasil Ed., Academic Press, N.Y., 1st Ed., (1983) and "Tissue Culture in the Production of Novel Disease-Resistant Crop Plants," *Biol. Rev.*, 54:329–345 (1975)).

These uses include selection at the cellular level of mutations for resistance to toxic substances, such as herbicides and substances produced by plant pathogens. Since the selections are carried out at the cellular level, it is likely that whole plants regenerated from the cells will show the selected characteristic. It is significant that such a system would allow plant breeders to select (or screen) for the desired characteristic from among thousands of cells in a single culture dish or flask, whereas a large field plot would be required to select or screen a corresponding number of seed grown plants according to traditional plant breeding methods.

It has, for example, been demonstrated that corn plants derived from Black Mexican Sweet corn, a non-commercial cultivar, can be regenerated from tissue cultures that have been selected for resistance to lysine and threonine and that tissues of the regenerated plant likewise produce corn plant tissue that is resistant to lysine and threonine. (See Hibberd, K. A. et al., "Selection and Characterization of a Feedback Insensitive Tissue Culture of Maize," *Planta*, 148:183–187 (1980).)

The utility of such selections carried out in callus cultures has also been demonstrated by the regeneration from callus culture of corn plants resistant to southern corn leaf blight, a plant disease caused by a pathotoxin produced by the plant pathogen *Helminthosporium maydis* race T. By exposing corn callus to the pathotoxin produced by the plant pathogen, resistant callus was selected. Significantly, the progeny of certain resistant plants were also resistant to the toxin and plant pathogen. Thus callus culture of a corn cell line is demonstrably effective in the development of pathogen resistant corn seed. (See Gengenbach et al., "Inheritance of Selected Pathotoxin Resistance in Maize Plants Regenerated From Cell Cultures," *Proc. Nat'l. Acad. Sci. USA*, 74:5113–5117 (1977)).

SUMMARY OF THE INVENTION

The present invention comprises tissue cultures of corn inbred line B73. These tissue cultures are characterized as embryogenic callus cultures of corn inbred B73 and cell suspension cultures derived from the embryogenic callus culture of corn inbred B73. B73 is used to include closely related lines such as LH119 and LH132.

DETAILED DESCRIPTION OF THE INVENTION

As used herein, the term "embryogenic callus" is defined as a callus with the potential to regenerate plants via somatic embryogenesis.

As used herein the term "variation" is defined as phenotypic changes that are: stable, i.e, they persist in the absence of the event that induced the change; and heritable, i.e., the new phenotype is transmitted to daughter cells when they divide. Changes in phenotype that persist only so long as the cells or tissues are maintained in a new environment are referred to as physiological responses.

"Genetic variation" is used herein to describe heritable variation that is sexually transmitted to progeny of plants regenerated from cultured cells or tissues. The term "mutant" is reserved for the special case of genetic variation in which a trait is transmitted meiotically according to well-established laws of inheritance. When the nature of the heritable change is not known, the term "variant" is used.

As used herein the term "regenerated", referring to plants means plants derived from cell and tissue culture. The term "progeny" means plants obtained by self-fertilization, sibling-fertilization, backcrossing or outcrossing of the regenerated plants.

As used herein the term "clone" refers to callus or cell suspensions propagated from an established cell suspension or callus line.

Typically, embryogenic callus of B73 consists of cells organized into masses of embryo-like structures, structures which can be discrete or fused into clusters. Various aspects of embryo development in vivo can be recognised in these calluses, for example organized growths resembling the scutellum are usually apparent. The callus can be maintained on agar-solidified MS-type medium supplemented with e.g. between 0.1 mg/l and 10.0 mg/l 2,4-D, preferably between 0.5 mg/l and 2.0 mg/l 2,4-D. 2,4-D is one example of an auxin which functions in this invention. Others include dicamba and picloram. Careful visual selection to ensure transfer of appropriate embryo-like structures is required for culture maintenance. Cultures are usually transferred at three to four-weekly intervals. Transfer of material other than that displaying embryogenic morphology results in loss of the ability to recover whole plants from the callus.

Embryogenic callus of B73 can spontaneously produce sectors of rapidly growing, visually homogeneous cell populations which can be maintained in a stable condition and which provide suitable material for the isolation of cell suspensions (cells growing suspended in agitated liquid medium). These latter cultures are referred to as embryogenic cell suspension cultures since they retain the potential to produce organized, recognizably embryogenic structures when returned to growth on appropriate culture medium solidified with agar.

Regeneration of whole plants from the embryogenic callus of B73 is accomplished by transfer of carefully selected embryogenic structures, either singly or in clusters, to a medium in which the concentration of 2,4-D has been reduced. The reduction in concentration is usually between one quarter and one half of what is present in the culture maintenance medium (e.g. 1.0 mg/l to 0.5 mg/l, or 0.5 mg/l to 0.25 mg/l).

A number of such steps is usually required (e.g. 1.0 mg/l to 0.5 mg/l to 0.25 mg/l to 0.1 mg/l) to complete whole plant regeneration with, at each step, a matching of the stage of embryo development or germination with the appropriate 2,4-D concentration so that the more mature structures are matched with the lower 2,4-D concentrations.

Complete removal of 2,4-D from the medium may be necessary to obtain adequate root growth from the resulting young plantlets of inbred B73. These plants can be transferred to soil and grown to maturity. The plants are usually fertile and yield seed progeny in the same ways as seed-grown B73 plants.

Therefore the invention includes corn plants regenerated from an embryogenic callus of corn inbred B73 and the progeny of the regenerated corn plants.

Embryogenic cell suspension cultures of corn inbred B73 can be obtained from friable callus cultures deriving from the embryogenic callus culture described above.

Friable callus is transferred into a medium suitable for initiating and maintaining a cell suspension culture, e.g. MS medium with between 0.5 mg/l and 5.0 mg/l 2,4-D, and is placed on a gyrotary shaker at 120 rpm at 27° C.

Dispersed cell suspensions, once obtained, can be induced to form embryos by first plating out on MS Medium solidified with agar and containing between 0.5 mg/l and 2.0 mg/l 2,4-D. After between two and four weeks callus is further transferred to solidified medium containing the same or a lower 2,4-D concentration. After a further 2 to 4 week period structures resembling embryos can be induced to develop by placing the callus on medium containing no 2,4-D or lower levels of 2,4-D. These embryos can subsequently germinate to produce plantlets.

Thus, the invention includes corn plants regenerated from an embryogenic cell suspension of corn inbred B73 and the progeny of the regenerated corn plants.

The ability to regenerate whole plants from the embryogenic tissue and cell suspension cultures of corn inbred B73 provided by the instant invention also enables those skilled in the art to carry out in vitro selections for desirable traits or against undesirable traits. (See Hibberd et al. and Gengenbach et al., both mentioned hereinabove.) Thus, using the embryogenic tissue or cell suspension cultures of corn inbred B73 of the instant invention, it is now possible to expose cultures of corn inbred B73 to selective agents for example herbicides and pathotoxins, to select tissues and cells resistant to the selective agents and to regenerate plants resistant to such selective agents. Thus, considered within the scope of the instant invention are embryogenic tissues and cells of corn inbred B73 selected in vitro, the corn plants and seed thereof regenerated therefrom and the progeny of the regenerated corn plants.

It will also be readily apparent to those skilled in the art that embryogenic tissue and cell suspension culture of corn inbred B73 provide the opportunity for the generation of somaclonal variants in corn inbred B73 by regenerating plants from embryogenic tissue culture and cell suspension cultures of corn inbred B73 provided by the instant invention. Such stable somaclonal variants are well known to those skilled in the art as exemplified in Edallo et al., "Chromosomal Variation and Frequency of Spontaneous Mutation Associated with the in vitro Culture and Plant Regeneration in Maize," *Maydica* 26, pp. 39-56 (1981); Becker et al., "Etude de la Variabilite Genetique Obtenue Chez le Mais Apres Callogenese et Regeneration de Plants in vitro, *Agronomie* 3, pp. 9-18 (1983); and Larkin et al., "Somaclonal Variation - A Novel Source of Variability from Cell Cultures for Plant Improvements," *Theor. Appl. Genet.* 60, pp. 197214 (1981). A large body of literature in fact suggests that plants regenerated from culture are characterized by an unexpectedly high rate of stable propagatable phenotypic variation. See Rice, "Tissue Culture Inbred Genetic Variation in Regenerated Maize Inbred, 37th Ann. Corn & Sorghum Research Conference (1983). Thus it is now possible to provide progeny with genetic variations arising from somaclonal variants regenerated from corn inbred B73. Such characteristics may be stably maintained in the second generation progeny of the regenerated plants and will generally exhibit either Mendelian segregation (e.g., 3:1 ratio for single gene traits), uniform expression (since somaclonal variations arises in diploid cells and may generate homozygous variants), or continuous phenotypic variation for quantitatively inherited traits (i.e. maturity and height). The majority of agronomically important traits upon which crop improvement depend are quantitatively inhereted. Thus, the invention is considered to encompass somaclonal variants of the embryogenic callus and cell suspension of corn inbred B73, corn plants and the seed thereof regenerated therefrom and the progeny of the regenerated corn plants. Line B73 has been deposited with the American Type Culture Collection, 12301 Parklawn Drive, Rockville, Md. 20852, receiving accession number 40239.

The examples to follow are illustrative and in no way limit the scope of the appended claims.

EXAMPLE 1

Initiation, selection and maintenance of an embryogenic callus culture of B73

Plants from Maize inbred line B73 were grown to flowering in a greenhouse supplemented with Lucalux high pressure sodium lights (16 hours/day) and maintained at 27° C. during the day and 16° C. at night. Plants were then self-pollinated. Immature zygotic embryos (0.5 mm to 2.0 mm in length, 9 to 14 days post-pollination) were aseptically removed from surface-sterilized kernels and placed flat side down on the initiation medium which contained MS salts, 0.5 mg/l thiamine, 0.9% (wt/vol) agar, 1.0 mg/l 2,4-D and 2% sucrose (culture medium had been adjusted to a pH of 6.0 prior to autoclaving). Cultures were incubated in the dark at 23° C. All culture manipulations and selections were performed with the aid of a dissecting microscope.

Initially, (after 5 to 7 days) outgrowths from the surface of the scutellum were observed. These outgrowths were smooth at their surface, reflective and globular in form. This is the initiation of the embryogenic callus. After between 7 and 21 days the outgrowths were cut from the immature embryo explant and were placed on fresh medium of the same composition. Alternatively, the immature embryo explant itself was placed on fresh medium to promote further development of the outgrowths prior to their excision and subculture.

Several subcultures later (after 2 to 3 months) there was enough material from some immature embryo explants for subdivision of this embryogenic callus into two or three or more pieces. There was no mixing of callus pieces from different immature embryo explants. After further growth and subculture (now 6 months after embryogenic callus initiation) there were between 50 and 100 pieces (each ca. 100 mg fresh weight) deriving ultimately from one selected immature embryo explant. During this time of culture expansion a characteristic embryogenic culture morphology developed as a result of careful selection at each subculture. Any organized structures resembling roots or root primordia were discarded. Any material known from experience to lack the capacity for sustained growth was also discarded (translucent, 'watery', embryogenic structures). Structures with a firm consistency, resembling at least in part the scutellum of the in vivo embryo were selected.

These so-called "scutellar" cultures could be maintained for periods of at least five years by careful visual selection at each monthly subculture on to fresh medium of the same composition as that used for culture initiation.

EXAMPLE 2

Initiation, Selection and Maintenance of a Friable, Rapidly Growing, Embryogenic Callus of B73

After approximately one year the "scutellar" cultures spontaneously produced sectors of friable, rapidly growing, pale yellow, apparently structureless callus. Upon close microscopic examination, minute (ca. 50 to 100 cells) globular embryos could be seen. These embryos developed from a matrix of visually uniform callus cells. Development, however, on this culture medium did not proceed beyond the early globular stage if the friable embryogenic callus was subcultured at two to three-week intervals. Care was taken at each subculture to exclude translucent "watery" sectors with no capacity for organised growth.

The friable, rapidly-growing embryogenic callus could be maintained for periods of at least six years by careful visual selection and by subculture at two to three-week intervals on to fresh medium of the same composition as that used for culture initiation.

EXAMPLE 3

Initiation and Maintenance of an Embryogenic Cell Suspension of B73. Recovery of Embryos and Plantlets from this Suspension One gram of the friable, rapidly growing embryogenic callus was inoculated into 20 ml of MS Medium having the following components:
magnesium sulfate-seven hydrate (mgSO$_4$.7H$_2$),
calcium chloride-dihydrate (CaCl$_2$.2H$_2$O),
potassium nitrate (KNOH$_3$),
ammonium nitrate (NH$_4$NO$_3$),
potassium phosphate (KH$_2$PO$_4$),
manganese sulfate-four hydrate (MnSO$_4$.4H$_2$O),
zinc sulfate-seven hydrate (ZnSO$_4$.5 H$_2$O),
cupric sulfate-five hydrate (CuSO$_4$.5 H$_2$O),
cobalt chloride-six hydrate (CoCl$_2$.6H$_2$O).
potassium iodide (KI),
boric acid (H$_3$BO$_3$),
sodium molybdinum oxide-dihydrate (Na$_2$MoO$_4$.2H$_2$O),
ferrous sulfate-seven hydrate (FeSO$_4$.7H$_2$), and
sodium ethylenediaminotetracetic acid (Na$_2$EDTA).
In general, as used in the invention, the exact concentration of the salts can be varied within limits without departing from the invention. To standardize the making of the media, however, the concentrations of the above listed minimal salts are as follows:

| | |
|---|---|
| MgSO$_4$.7H$_2$O | 370 milligrams/liter (mg/l) |
| CaCl$_2$.2H$_2$O | 440 mg/l |
| KNO$_3$ | 1900 mg/l |
| NH$_4$NO$_3$ | 1650 mg/l |
| KH$_2$PO$_4$ | 170 mg/l |
| MnSO$_4$.4H$_2$O | 22.3 mg/l |
| ZnSO$_4$.7H$_2$O | 8.6 mg/l |
| COSO$_4$.5H$_2$O | 0.025 mg/l |
| CoCl$_2$.6H$_2$O | 0.025 mg/l |
| KI | 0.83 mg/l |
| H$_3$BO$_3$ | 6.2 mg/l |
| Na$_2$MoO$_4$.2H$_2$O | 0.25 mg/l |
| FeSO$_4$.7H$_2$O | 28.75 mg/l |
| Na$_2$EDTA | 37.25 mg/l |

The medium further contains the following vitamins, hormones and carbohydrate sources:

| | |
|---|---|
| Thiamine HCL | 0.5 mg/l |
| 2,4-D | 1.0 mg/l |
| sucrose | 2% wt/vol |
| pH | 6.0 |

The callus and medium, in a 125 ml wide-mouth Erlenmeyer flask are incubated 27° on a gyrotary shaker at 120 rpm in the dark or in the presence of low light (2 to 10 umoles/meter$^{-2}$/sec$^{-1}$).

The resultant suspension culture can be transferred once every seven days by taking 5 to 10 ml of the culture and introducing this inoculum into 20 ml of fresh medium of identical composition to that listed.

To recover embryos from these cultures 5 to 10 ml of the culture is placed on the surface of medium of identical composition as that listed (except that it is solidified by addition of 0.9% wt/vol agar). After three weeks all callus material is transferred to fresh medium of identical composition. After a further three weeks, structures resembling embryos were induced to develop by placing the callus on medium containing a lower level of 2,4-D (e.g. 0.5 mg/l or 0.25 mg/l). Plantlets were regenerated from these embryos by transfer to a hormone-free medium.

EXAMPLE 4

Regeneration of B73 Plants from Embryogenic Callus Culture

Pieces of scutellar culture (example 1) of approximately 100 mg fresh weight were taken and transferred to fresh medium identical to culture initiation and maintenance medium except for containing 0.5 mg/l 2,4-D. This culture was then placed in the light (1000 to 2000 lux, Sylvania - cool white), for 16 hours a day. Uner these conditions the scutellar structures underwent elongation and greening. Further elongation can be promoted by transfer after three to four weeks to the same medium except now containing only 0.25 mg/l 2,4-D. Plantlet production (formation of a shoot and root) may occur on this medium or, after another transfer to medium containing only 0.1 mg/l 2,4-D, may be required.

Further growth of the plantlets is promoted by transfer to medium containing no 2,4-D. PlantCons (Flow Labs), containing 100 ml of medium, are suitable containers for this step. Several hundred plants have been regenerated using this method. They have been transferred to pots in the greenhouse and grown to maturity.

EXAMPLE 5

Of the plants obtained in Example 4 seventy set seed when either self-pollinated (designated R1S1), backcrossed to the parent B73 line (designated R1BC1) or sibbed (designated R1×R1).

The seeds produced were grown out in the field in Groton, Conn., and Windfall, Ind., in the spring and summer of 1981. The progenies subsequently obtained from these plantings have been the subject of extensive evaluation, an evaluation which is continuing at the present time.

Progeny with genetic variation arising from somaclonal variants regenerated from corn inbred B73 have been obtained.

We claim:

1. An embryogenic culture derived from inbred corn line B73, wherein said culture is selected from the group consisting of embryogenic callus, embroygenic cell suspensions, clones of said embroygenic callus, and clones of said embryogenic cell suspensions.

2. The embryogenic culture of claim 1 further defined as comprising mutations.

3. The embryogenic culture of claim 1 further defined as having a diploid chromosome complement.

* * * * *